(12) United States Patent
Ionson

(10) Patent No.: US 9,349,098 B1
(45) Date of Patent: May 24, 2016

(54) COGNITIVE MEDICAL AND INDUSTRIAL INSPECTION SYSTEM AND METHOD

(71) Applicant: James Albert Ionson, Lexington, MA (US)

(72) Inventor: James Albert Ionson, Lexington, MA (US)

( * ) Notice: Subject to any disclaimer, the term of this patent is extended or adjusted under 35 U.S.C. 154(b) by 0 days.

(21) Appl. No.: 14/712,718

(22) Filed: May 14, 2015

(51) Int. Cl.
  *G06N 5/00* (2006.01)
  *G06F 1/00* (2006.01)
  *G06N 5/04* (2006.01)
  *G06N 7/00* (2006.01)

(52) U.S. Cl.
  CPC ... *G06N 5/04* (2013.01); *G06N 7/00* (2013.01)

(58) Field of Classification Search
  CPC ......... G06N 7/005; G06N 5/048; G06N 5/04; G06Q 50/01
  See application file for complete search history.

(56) References Cited

U.S. PATENT DOCUMENTS

| 2008/0004904 | A1* | 1/2008 | Tran | A61B 5/0006 705/2 |
| 2015/0125832 | A1* | 5/2015 | Tran | G09B 5/00 434/127 |
| 2015/0294086 | A1* | 10/2015 | Kare | G06F 19/3481 705/3 |

* cited by examiner

Primary Examiner — Stanley K Hill
Assistant Examiner — Kalpana Bharadwaj

(57) ABSTRACT

The present invention relates to inspection of medical patients including, but not limited to, phonocardiography, auscultation and ultrasound medical imaging and other non-acoustical inspection techniques; and industrial non-destructive testing and evaluation of materials, structural components and machinery; and more particularly to the incorporation of cognitive artificial intelligence into an inspection system and method that utilizes cognitive mathematical techniques which emulate the cognitive processing abilities of the human brain including, but not limited to, symbolic cognitive architectures and inference process algebras, to analyze data collected from infrasound acoustical sensors (0.1 Hz-20 Hz), audible acoustical sensors (20 Hz to 20 kHz), ultrasound acoustical sensors and transmitters above 20 kHz, data collected from other non-acoustical inspection devices and systems including, but not limited to electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data); fuse this data resulting in the generation of new metadata; and then utilize cognitive mathematical techniques to interpret this data against inspection signatures that characterize conditions being diagnosed. The present invention has the ability to also identify and anticipate abnormal conditions that fall outside known inspection signature patterns; and communicate the inspection results to an operator thereby simplifying the initial inspection and diagnosis for medical patients and industrial objects; minimizing false negative and false positive initial inspection results and lowering costs.

16 Claims, 1 Drawing Sheet

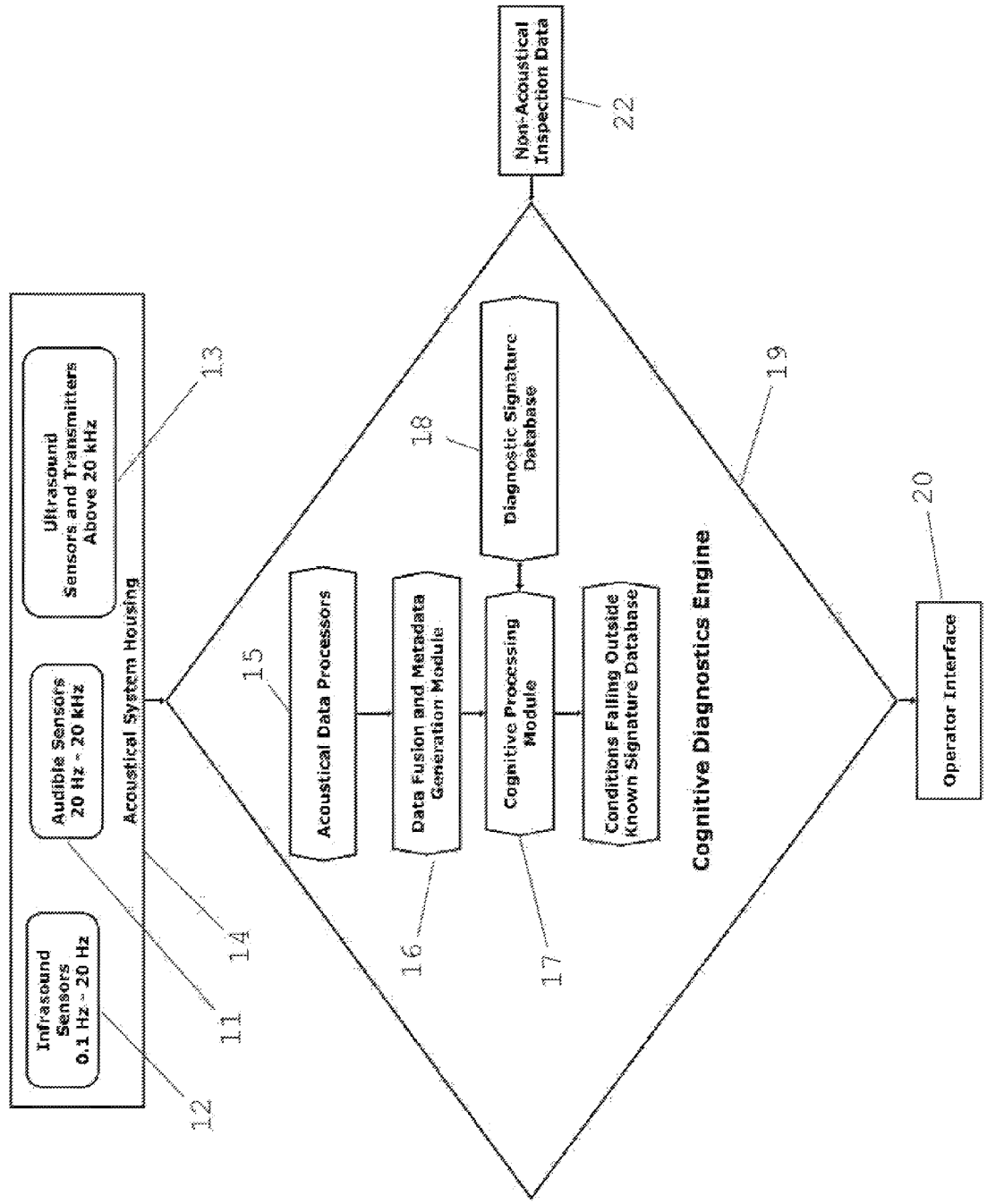

COGNITIVE MEDICAL AND INDUSTRIAL INSPECTION SYSTEM AND METHOD

RELATED APPLICATIONS

The present application is related to U.S. Pat. No. 8,892,196, issued Nov. 18, 2014, for DEVICE AND METHODDFOR SCREENING CONGENITAL HEART DISEASE, by Chang; Ruey-Kang, included by reference herein.

The present application is related to U.S. Pat. No. 8,856,057, issued Oct. 7, 2014, for COGNITIVE SECURITY SYSTEM AND METHOD, by James A. Ionson, included by reference herein.

The present application is related to U.S. Pat. No. 8,764,660, issued Jul. 1, 2014, for METHODS AND APPARATUS FOR COMBINED AUDIBLE AND ULTRASOUND INSPECTION OF OBJECTS, INCLUDING PATIENTS, by Frigstad; Sigmund, Gelly; Jean-Francois, Torp; Hans Garmann, included by reference herein.

The present application is related to U.S. Pat. No. 8,494,829, issued Jul. 23, 2013, for SENSOR FUSION AND PROBABILISTIC PARAMETER ESTIMATION METHOD AND APPARATUS, by Teixeira; Rodrigo E., included by reference herein.

The present application is related to U.S. Pat. No. 7,483,867, issued Jan. 27, 2009, for PROCESSING DEVICE WITH INTUITIVE LEARNING CAPABILITY, by Ansari, Arif M; Ansari, Shiek; Sulaimann, Yusuf M., included by reference herein.

The present application is related to U.S. Pat. No. 7,393,326, issued Jul. 1, 2008, for APPARATUS FOR SCREENING AND DIAGNOSING BY DUAL STETHOSCOPIC AND DOPPLER DETECTION, by Bindefeld, Herve, included by reference herein.

The present application is related to U.S. Pat. No. 5,490,516, issued Feb. 13, 1996, for METHOD AND SYSTEM TO ENHANCE MEDICAL SIGNALS FOR REAL-TIME ANALYSIS AND HIGH-RESOLUTION DISPLAY, by Hutson; William H., included by reference herein.

The present application is related to U.S. Pat. No. 5,218,969, issued Jun. 15, 1993, for INTELLIGENT STETHOSCOPE, by Bredesen, Mark S.; Schmerler, Elliot D., included by reference herein.

The present application is related to U.S. Pat. No. 5,025,809, issued Jun. 25, 1991, for RECORDING, DIGITAL STETHOSCOPE FOR IDENTIFYING PCG SIGNATURES, by Johnson, Keith H.; Underwood, David A., included by reference herein.

The present application is related to U.S. Pat. No. 4,922,917, issued May 8, 1990, for ULTRASONIC TISSUE CHARACTERIZATION, by Dory; Jacques, included by reference herein.

This application claims the benefit of U.S. Provisional Application No. 62/142,211, filed Apr. 2, 2015 which is incorporated herein by reference in their entirety for all purposes.

OTHER PUBLICATIONS

Federico Castanedo, "A Review of Data Fusion Techniques", The Scientific World Journal, Vol 2013, Article ID 704504, 2013.

Prashant Kumar et al, "Signal Processing Apparatus and Method for Phonocardiogram Signal", USPTO Publication #20120289849.

Clarence Shub, "Echocardiography or Auscultation? How to Evaluate Systolic Murmurs", Canadian Family Physician, Vol. 49, February 2003.

T. Xie et al, "Rapid Screening of Cardiac Patients with a Miniaturized Hand-held Ultrasound Imager—Comparisons with Physical Examination and Conventional Two-Dimensional Echocardiography", Clin Cardiol 27/4:241-5, April 2004.

Kotler et al, "Echocardiographic and Phoncardiographic Correlation of Heart Sounds and Mumurs", Cardiovasc Clin. 1978.

John E. Laird, "The SOAR Cognitive Architecture", MIT Press, May 2012.

R. Salemi et al, "Noninvasive Graphic Evaluation: Phonocardiography and Echocardiography", Cardiovasc Clin. 1986.

Salah M. Ali Al-Obaidi, M. Salman Leong, R. I. Raja Hamzah and Ahd. M. Abdelrhman, "A Review of Acoustic Emission Technique for Machinery Condition Monitoring; Defects Detection & Diagnostic", Applied Mechanics and Materials Vols. 229-231 00 1476-1480, Trans Tech Publications, Switzerland, 2012.

Sigmund Frigstad and Bjorn Olstad, "Method and Apparatus for Knowledge based Diagnostic Imaging", USPTO Publication #20050010098.

Peter Jackson, "Introduction to Expert Systems (3rd Edition) Hardcover", Dec. 23, 1998.

Patrick Soon-Shiong, "Reasoning Engines", USPTO Publication #20140129504, May 2014.

Nikolaos Anastasopoulos, "Systems and Methods for Artificial Intelligence Decision Making in a Virtual Environment", USPTO Publication #20140279800.

Nils Goerke, "EMOBOT: A Robot Control Architecture Based on Emotion-Like Internal Values", Mobile Robots, Moving Intelligence (ed J. Buchli). ARS/pIV, Germany, 75-94, 2006.

M. Salichs and M. Makfaz, "Using Emotions on Autonomous Agents. The Role of Happiness, Sadness and Fear" Adaptation in Artificial and Biological Systems (AISB'06), Bristol, England, 157-164, 2006.

Eugene Eberbach, "$-Calculus of Bounded Rational Agents: Flexible Optimization as Search under Bounded Resources in Interactive Systems", Fundamentalnformaticae 68, 47-102, 2005.

Eugene Eberbach, "$-Calculus Bounded Rationality=Process Algebra+Anytime Algorithms", Applicable Mathematics: Its Perspectives and Challenges, Narosa Publishing House, New Delhi, Mumbai, Calcutta, 532-539, 2001.

Eugene Eberbach and Shashi Phoha, "SAMON: Communication, Cooperation and Learning of Mobile Autonomous Robotic Agents, Proc. of the 11th IEEE. Conf. on Tools with Artificial Intelligence ICTAI'99, Chicago, Ill., 229-236, 1999.

Bradley J. Harnish, "Reactive Sensor Networks (RSN)", AFRL-IF-RS-2003-245 Technical Report, Penn State University sponsored by DARPA and AFRL, 2003.

Carlos Gershenson, "Behaviour-based Knowledge Systems: An Epigenetic Path from Behaviour to Knowledge", http://cogprints.org/2320/3/Gershenson-BBKS-Epigenetics.pdf.

Leonid I. Perlovsky, "Sapience, Consciousness, and the Knowledge Instinct. (Prolegomena to a Physical Theory)", In Sapient Systems, Eds. Mayorga, R, Perlovsky, L. I., Springer, London, 2007.

Leonid I. Perlovsky, "Modeling Field Theory of Higher Cognitive Functions", Chapter III in "Artificial Cognition Systems, Eds. A. Loula, R. Gudwin, J. Queiroz. Idea Group, Hershey, Pa., pp. 64-105, 2006.

Jitesh Dundas and David Chik, "Implementing Human-Like Intuition Mechanism in Artificial Intelligence", http://www.arxiv.org/abs/1106.5917, Jun. 29, 2011.

FIELD OF THE INVENTION

The present invention relates to inspection of medical patients including, but not limited to, phonocardiography, auscultation and ultrasound medical imaging and other non-acoustical inspection techniques; and industrial non-destructive testing and evaluation of materials, structural components and machinery; and more particularly to the incorporation of cognitive artificial intelligence into an inspection system and method that utilizes mathematical techniques which emulate the cognitive processing abilities of the human brain including, but not limited to, symbolic cognitive architectures and inference process algebras, to analyze data collected from infrasound acoustical sensors (0.1 Hz-20 Hz), audible acoustical sensors (20 Hz to 20 kHz), ultrasound acoustical sensors and transmitters above 20 kHz, data collected from other non-acoustical inspection devices and systems including, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data); fusing this data resulting in the generation of new metadata; and then utilizing cognitive artificial intelligence technology to interpret this data against inspection signatures that characterize conditions being diagnosed. The present invention has the important ability to also anticipate abnormal conditions that fall outside known inspection signature patterns; and communicate the inspection results to an operator for the purpose of quickly analyzing, interpreting and managing the overall inspection process.

BACKGROUND OF THE INVENTION

A major deficiency of inspection systems and methods for, but not limited to, medical inspection such as phonocardiography, auscultation and ultrasound imaging and other non-acoustical medical inspection techniques; industrial non-destructive inspections such as passive acoustical emission (including ultrasound emission), active ultrasound inspection techniques and other non-acoustical inspection techniques, is that multiple independent devices must be utilized requiring multiple highly experienced operators skilled in the use and interpretation of inspection data obtained from these different devices. For example, medical phonocardiography, auscultation and ultrasound imaging, as well as industrial acoustical emission and ultrasound testing of industrial objects utilize devices that operate in a variety of different frequency domains ranging from infrasound (0.1 Hz-20 Hz), audible (20 Hz-20 kHz) and ultrasound (20 kHz up to many MHz). Each device operating in their own respective frequency range provides select acoustical data to a highly skilled operator with the trained ability to interpret the acoustical data based upon unique acoustical signatures characteristic of conditions being diagnosed for a particular application within a particular frequency range. Effective acoustical inspection and diagnosis of conditions therefore requires multiple devices and multiple highly trained operators which adds expense and complexity to the overall inspection process. This problem is compounded with the inclusion of additional data collected from other non-acoustical devices and systems including, but not limited to electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data) requiring additional experts skilled in the integrated, multi-data diagnosis of medical patients and industrial objects.

An attempt to simplify acoustical inspection involving the combination of audible and ultrasound systems into a single device is disclosed in U.S. Pat. No. 8,764,660, "Methods and Apparatus for Combined Audible and Ultrasonic Inspection of Objects, Including Patients" incorporated herein by reference in its entirety. However, this referenced disclosure only describes an apparatus that is in essence two independent acoustical devices packaged within the same housing; and although they can operate simultaneously, the acoustical data from these two devices are independently displayed with analysis and interpretation performed "manually" by the operator, and only as effective as the operator's skill and training in the analysis and interpretation of independent acoustical data sets collected from different acoustical collection modalities. The collected acoustical data is therefore "fused" organically based upon the operator's data interpretation skills and not by computational data fusion processing performed within the device through mathematical algorithms and digital techniques. Data fusion through digital processing of different data sets brings together all data and attributes into a single view; and generates new metadata that provides a far more complete and informative set of inspection data that is representative of the medical patient or industrial object (e.g., "A Review of Data Fusion Techniques"; U.S. Pat. No. 5,490,516, "Method and System to Enhance Medical Signals for Real-Time Analysis and High-Resolution Display"; U.S. Pat. No. 8,494,829, "Sensor Fusion and Probabilistic Parameter Estimation Method and Apparatus"; all incorporated herein by reference in their entirety). The final analysis of the fused data, however, is still performed manually by operators who must be highly trained in order to properly interpret the result and generate an accurate diagnosis. There have been other disclosures related to using various data correlation techniques that are designed to compare collected data with a database of known conditions thereby assisting relatively inexperienced operators with proper interpretation of the data (e.g., U.S. Pat. No. 5,218,969, "Intelligent Stethoscope"; U.S. Pat. No. 8,892,196, Device and Method for Screening Congenital Heart Disease"; U.S. Pat. No. 5,025,809, Recording, Digital Stethoscope for Identifying PCG Signatures"; USPTO Publication #20120289849, "Signal Processing Apparatus and Method for Phonocardiogram Signal"; USPTO Publication #20050010098, "Method and Apparatus for Knowledge Based Diagnostic Imaging", all incorporated herein by reference in their entirety); however, these systems and methods can lead to multiple false negative diagnostic results since these systems and methods are based primarily upon rule-based models and probabilistic algorithms, all of which break down when data patterns fall outside of known signature patterns contained within a pre-programmed data base of possible conditions being diagnosed.

Therefore, there is a need for medical and industrial inspection systems and methods to be more fully integrated across a range of acoustical frequencies from the sub-audible through the ultrasound range of frequencies, with the ability to fuse all of the collected acoustical data with other provided non-acoustical inspection data resulting in the generation of new metadata which can then be interpreted and diagnosed by cognitive artificial intelligence techniques against known inspection signatures characterizing conditions being diagnosed with the ability to also anticipate abnormal conditions that fall outside known signature patterns; and communicate the integrated inspection results to an operator for the purpose of analyzing, interpreting and managing the overall inspection process. This system and method enables less skilled operators with a cognitive tool that emulates a diagnosis performed by multiple highly trained operators skilled in data interpretation from multiple inspection devices, thereby lowering costs, simplifying the initial inspection and diagnosis for medical patients and industrial objects and minimizing the possibility of initial false negative and false positive interpretations.

SUMMARY OF THE INVENTION

In accordance with the present invention, there is provided a cognitive inspection system and method used for, but not limited to, the inspection of medical patients and industrial objects which incorporates cognitive artificial intelligence through the utilization of mathematical techniques that emulate the cognitive processing abilities of the human brain including, but not limited to, symbolic cognitive architectures and inference process algebras, to process and interpret fused acoustical data from infrasound sensors (0.1 Hz-20 Hz), audible acoustical sensors (20 Hz to 20 kHz), ultrasound acoustical sensors and transmitters (greater than 20 kHz), data from other non-acoustical inspection devices and systems including, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data); and interprets this fused inspection data and newly generated metadata against known signatures characterizing conditions being diagnosed with the ability to also anticipate abnormal conditions that fall outside known signature patterns; and communicate the inspection results to an operator for the purpose of analyzing, interpreting and managing the overall inspection process. The provided cognitive inspection system and method enables less skilled operators the ability to perform an inspection and diagnosis of medical patients and industrial objects that emulates a similar inspection and diagnosis performed by multiple highly trained operators skilled in data interpretation from multiple inspection devices, thereby lowering costs, simplifying the initial inspection and diagnosis for medical patients and industrial objects and minimizing false negative and false positive initial inspection results.

The provided cognitive inspection system and method comprises at least one acoustical sensor, at least one acoustical transmitter and at least one electronic processor located in a common housing. The acoustical sensors and transmitters operate in the infrasound acoustical range (0.1 Hz-20 Hz), audible acoustical range (20 Hz-20 kHz) and the ultrasound range (greater than 20 kHz) with the collected raw acoustical data digitally processed by at least one digital processor either within or external to the housing. Processed acoustical data, other non-acoustical inspection data, and combinations thereof, are further processed either within or external to the housing through data fusion techniques resulting in the generation of additional metadata which is then analyzed by cognitive mathematical techniques that emulate the cognitive processing powers of the human brain including, but not limited to, symbolic cognitive architectures (e.g., "The SOAR Cognitive Architecture" which is incorporated herein by reference in its entirety) and inference process algebras such as, but not limited to $-calculus (pronounced: "cost calculus") (e.g., "$-Calculus of Bounded Rational Agents" which is incorporated herein by reference in its entirety). The purpose of the cognitive analysis is to interpret the fused inspection data and newly generated metadata against a database of known signatures that characterize conditions being diagnosed, with the ability to also anticipate abnormal conditions that fall outside known signature patterns. The cognitive analysis is performed by a cognitive processing module located within or external to the housing and uses cognitive mathematical techniques to simulate the "emotional state" of the system such as "happiness" when the fused inspection data and metadata exhibit patterns that are consistent with at least one diagnostic signature contained within a database of signatures characteristic of conditions being diagnosed; and "suspicion" when the inspection data is not consistent with any signatures contained within the database (e.g., "Using Emotions on Autonomous Agents. The role of Happiness, Sadness and Fear" which is incorporated herein by reference in its entirety). Cognitive mathematical techniques including, but not limited to, symbolic cognitive architectures and inference process algebras strive to minimize "suspicion" and maximize "happiness" leading to an initial diagnosis that minimizes false positive as well as false negative results to a system operator through a wired and/or wireless interface.

Therefore the provided cognitive inspection system and method enables less skilled operators with an integrated inspection system that emulates a diagnosis performed by multiple highly trained operators skilled in inspection data interpretation from multiple acoustical devices, other non-acoustical devices and systems including but not limited to electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data). The present invention lowers costs, simplifies the initial inspection and diagnosis for medical patients and industrial objects, and minimizes false negative and false positive diagnostic results.

BRIEF DESCRIPTION OF THE DRAWINGS

A complete understanding of the present invention may be obtained by reference to the accompanying drawings, when considered in conjunction with the subsequent, detailed description, in which:

FIG. 1 is a block diagram of a cognitive inspection system which combines cognitive artificial intelligence with fused infrasound sensor data in the 0.1 Hz-20 Hz frequency range, audible acoustical sensor data in the 20 Hz to 20 kHz frequency, ultrasound acoustical active and passive data above 20 kHz, data collected from other non-acoustical inspection devices and systems including, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data; and interprets this fused data and newly generated metadata against known signatures that characterize conditions being diagnosed with the important additional ability to anticipate abnormal conditions that fall outside known signature patterns; and communicate the inspection results to an operator for the purpose of analyzing, interpreting and managing the overall inspection process.

For purposes of clarity and brevity, like elements and components will bear the same designations and numbering throughout the FIGURE.

DESCRIPTION OF THE PREFERRED EMBODIMENT

To provide an overall understanding certain illustrative embodiments will be described; however, it will be understood by one skilled in the art of inspection devices for medical and industrial applications; and skilled in the art of data fusion and cognitive artificial intelligence that the system and method described can be adapted and modified to provide systems and methods for other suitable applications and that additions and modifications can be made without departing from the scope of the system and method described herein.

FIG. 1 is a block diagram of a cognitive inspection system which combines cognitive artificial intelligence with fused infrasound sensor data in the 0.1 Hz-20 Hz frequency range, audible acoustical sensor data in the 20 Hz to 20 kHz frequency, ultrasound acoustical active and passive data above 20 kHz, data collected from other non-acoustical inspection devices and systems including, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data. Cognitive mathematical techniques are utilized to interpret this fused data and newly generated metadata against known signatures that characterize conditions being diagnosed with the ability to also anticipate abnormal conditions that fall outside known signature patterns. The cognitive inspection results are communicated to an operator for the purpose of analyzing, interpreting and managing the overall inspection process.

The primary function of this invention is to provide less skilled operators with an cognitive medical and industrial inspection system that emulates a diagnosis performed by multiple highly trained operators skilled in data interpretation from multiple acoustical and non-acoustical inspection devices, thereby lowering costs, simplifying the initial inspection and diagnosis for medical patients and industrial objects; and minimizing the possibility of false negative and false positive interpretations. This is accomplished through an operator interface 20 which is integrated with a cognitive diagnostics engine 19 comprising a combination of acoustical infrasound sensors 12 operating in the 0.1 Hz-20 Hz frequency range, acoustical audible sensors 11 operating in the 20 Hz-20 kHz range, acoustical ultrasound sensors and transmitters 13 operating above 20 kHz, acoustical data processors 15, a data fusion and metadata generation module 16, a diagnostic signature database 18 and a cognitive processing module 17. The cognitive diagnostics engine 19 receives data inputs from acoustical infrasound sensors 12, acoustical audible sensors, acoustical ultrasound sensors and transmitters 13 operating above 20 kHz, non-acoustical inspection data 22 from peripheral devices and systems such as, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data, and combinations thereof. In one embodiment of this invention all acoustical components are housed within a single acoustical system housing 14 that is compact and which can be easily carried and operated by an operator. Infrasound and audible acoustical sensors can include, but are not limited to, high impedance solid/liquid sensors such as accelerometers, hydrophones, geophones or combinations thereof; and/or lower impedance air sensors that utilize microphones based upon a variety of sensing technologies such as capacitive, electrostatic, piezoelectric, flexural resonant technologies including those related to capacitive and electrostatic microelectromechanical systems (MEMS). Ultrasound sensors and transmitters include, but are not limited to, single/multiple piezoelectric crystals and or layers and/or arrayed capacitive/electrostatic micromachined ultrasound transducers (CMUT). Non-acoustical inspection data 22 is generated by devices and systems including, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data). Raw acoustical data from acoustical sensors and transmitters are initially processed by at least one acoustical data processor 15 which prepares the collected acoustical data for fusion with non-acoustical inspection data 22, and combinations thereof, with the generation of additional metadata accomplished by a data fusion and metadata generation module 16.

There are a number of data fusion techniques that have been reviewed and disclosed such as "A Review of Data Fusion Techniques"; U.S. Pat. No. 5,490,516, "Method and System to Enhance Medical Signals for Real-Time Analysis and High-Resolution Display"; U.S. Pat. No. 8,494,829, "Sensor Fusion and Probabilistic Parameter Estimation Method and Apparatus", all incorporated herein by reference in their entirety; and all of these techniques are designed to fuse different data sets through specialized digital processing which brings together all data and attributes into a single view. The newly generated metadata provides a far more complete and informative set of inspection data that is representative of the medical patient or industrial object. This fused inspection data and metadata is received by a cognitive processing module 17 which performs cognitive analysis and interpretation through mathematical techniques that emulate the cognitive processing abilities of the human brain including, but not limited to, symbolic cognitive architectures and inference process algebras; and interprets the results against a diagnostic signature database 18 characterizing conditions being diagnosed with the ability to also anticipate abnormal conditions that fall outside known signature patterns. Some examples of diagnostic signatures are described by Clarence Shub, "Echocardiography or auscultation? How to evaluate systolic murmurs", Canadian Family Physician, Vol. 49, February 2003; Xie et al, "Rapid Screening of cardiac patients with a miniaturized hand-held ultrasound imager—comparison with physical examination and conventional two-dimensional echocardiography", Clin Cardiol 27/4:241-5, April 2004; Salah M. Ali Al-Obaidi, M. Salman Leong, R. I. Raja Hamzah and Ahd. M. Abdelrhman, "A Review of Acoustic Emission Technique for Machinery Condition Monitoring; Defects Detection & Diagnostic", Applied Mechanics and Materials Vols. 229-231 00 1476-1480, Trans Tech Publications, Switzerland, 2012 which are all incorporated herein by reference in their entirety.

Most artificial intelligence methods focus on logical decision making and learning approaches based upon logical causes and effects related to past experiences and known scenarios which greatly limits their effectiveness and decision accuracy when faced with incomplete and/or uncertain data. These techniques typically incorporate logical decision-making and learned behavior through the use of pre-programmed databases and logical rules used by expert systems to enable autonomous decisions. These approaches are based upon logical reasoning rules such as deductive reasoning, abductive reasoning, cause-based reasoning, inductive reasoning, metaphorical mapping and fuzzy logic (e.g. "Introduction to Expert Systems", "Processing Device with Intuitive Learning Capability"; "Reasoning Engines"; "Systems and Methods for Artificial Intelligence Decision Making in a Virtual Environment", which are incorporated herein by reference in their entirety). The aforementioned artificial intelligence methods, which are based upon logic-driven models, rules and algorithms, have a major flaw in that they all break down when the collected inspection data patterns fall outside of expected parameters and logical rules thereby leading to numerous false positive and false negative interpretations. Therefore, in accordance with the present invention, the cognitive processing module 17 utilizes a form of artificial intelligence that overcomes these limitations and is capable of dealing with incomplete and uncertain information; and in particular can anticipate abnormal conditions that fall outside known signature patterns. Many embodiments of the present invention utilize symbolic cognitive architectures and inference process algebras (e.g., "Sapience, Consciousness, and the Knowledge Instinct. (Prolegomena to a Physical Theory)"; "Modeling Field Theory of Higher Cognitive Functions"; "Implementing Human-Like Intuition Mechanism in Artificial Intelligence"; "Behavior-Based Knowledge Systems: An Epigenetic Path from Behaviour to Knowledge"; "$-Calculus Bounded Rationality=Process Algebra+Anytime Algorithms"; "$-Calculus of Bounded Rational Agents: Flexible Optimization as Search under Bounded Resources in Interactive Systems"; "Using Emotions on Autonomous Agents. The role of Happiness, Sadness and Fear"; "EMOBOT: A Robot Control Architecture Based on Emotion-Like Internal Values"; "Modeling Field Theory of Higher Cognitive Functions"; "Implementing Human-Like Intuition Mechanism in Artificial Intelligence"; "Behavior-Based Knowledge Systems: An Epigenetic Path from Behaviour to Knowledge" which are all incorporated herein by reference in their entirety). Symbolic cognitive architectures and inference process algebras have built-in cost optimization mechanisms allowing them to deal with nondeterminism, incomplete and uncertain information. For example, $-calculus is a higher-order polyadic process algebra with a "cost" utility function, such as the probability that collected inspection data has some has some kind of correlated or un-correlated relationship with particular inspection data patterns. These cognitive artificial intelligence techniques have never been utilized by systems that inspect medical patients or industrial objects, however, they have been successfully applied to the Office of Naval research SAMON robotics testbed to derive GBML (Generic Behavior Message-passing Language) for behavior planning, control and communication of heterogeneous Autonomous Underwater Vehicles (AUV's) operating in hostile and unpredictable environments (e.g., SAMON: Communication, Cooperation and Learning of Mobile Autonomous Robotic Agents which is incorporated herein by reference in its entirety); and $-calculus has also been used in the DARPA Reactive Sensor Networks Project at ARL Penn. State university for empirical cost profiling (e.g., "Reactive Sensor Networks (RSN)" which is incorporated herein by reference in its entirety). The cognitive processing module 17 therefore operates using an internal value system that is not only dependent on the inspection data received by the data fusion and metadata generation module 16 but in addition depends upon metastates of the environment associated with unforeseen changes and/or conditions that lie outside the baseline inspection signatures contained within the diagnostic signature database 18. These internal values are designed in accordance with psychological terms that we (human beings) associate with "drives" and "curiosity". These internal values do not actually realize real "drives" and "curiosity", but the cognitive processing module 17 is designed in such a way that it exhibits behavior that emulates how highly trained and experienced human operators would use intuition and instinct combined with logical reasoning to analyze fused inspection data that may or may not be fully correlated or fully anti-correlated with diagnostic signatures contained within the diagnostic signature database 18. For example, one of the cost functions used by the cognitive processing module 17 could be "uncertainty" that the fused inspection data and metadata do not provide an exact match to any signatures contained within the diagnostic signature database 18. The cognitive processing module 17 therefore works to minimize cost expressions such as "uncertainty", "suspicion" and/or "fear" in a manner that simulates the cognitive processing abilities of multiple highly trained human operators given the same conditions.

The cognitive diagnostics engine 19 is able to provide cognitive inputs through a wired and/or wireless operator interface 20 to a lesser skilled operator thereby enabling an initial diagnosis that emulates a diagnosis performed by multiple highly trained operators skilled in data interpretation from multiple inspection devices and systems. This invention therefore simplifies the initial inspection and diagnosis for medical patients and industrial objects and minimizes false negative and false positive interpretations resulting in a more thorough and reliable initial diagnosis at lower overall cost.

Technical effects of at least one embodiment of the present invention include the data from multiple inspection modalities ranging from infrasound, through audible sound and into ultrasound—both active and passive, as well as other non-acoustical inspection data collected by external devices and systems including, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data. For example, in one embodiment a medical professional would be able to perform phonocardiography, auscultation and ultrasound imaging with a single physically and electronically integrated device; input additional non-acoustical inspection data collected by other devices and systems; and because of the invention's data fusion and cognitive processing capabilities, the medical professional would be able to quickly render an accurate initial diagnosis that would normally require consultation with multiple experts skilled in integrated data interpretation from multiple inspection devices.

Inspection of industrial objects is both passive (acoustical emission) and active (ultrasound) and utilizes multiple acoustical testing devices with frequencies ranging from 30 kHz to over 50 MHz, as well as other non-acoustic testing techniques including, but not limited to, electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data). Industrial objects that are typically tested for possible failure and/or weaknesses can be static, such as pressure vessels, pipe-lines and many other machinery and structural components used in the engineering industry; and condition monitoring of rotating machinery such as turbines and engines. For these industrial applications one embodiment of the present invention would enable an operator to perform multiple acoustical inspections with a single integrated device, fuse the collected acoustical data with other non-acoustical data that is imputed into the system; and perform a cognitive analysis of this fused inspection data providing a less skilled operator with a low cost, reliable analysis of the object being inspected.

Another embodiment of the present invention displays the fused data and metadata in a fully integrated audiovisual format that enables operators with the ability to interpret the fused data and metadata audibly as well as visually. Although only acoustical emissions between 20 Hz and 20 kHz are audible, the cognitive diagnostics engine 19 can also convert inaudible acoustical emissions as well as non-acoustical data (e.g., ultrasound imagery) into a simulated audible format which represents conditions being diagnosed. This simulated audio data representation enables at least one operator to analyze, interpret and manage the overall inspection process through an operator interface 20 that is wired and/or wireless.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A cognitive medical and industrial inspection system and method for providing cognitive inspection of medical patients and industrial objects, comprising:

means for performing cognitive analysis and diagnosis of fused acoustical, non-acoustical, and combinations thereof, inspection data through the use of mathematical techniques that emulate the cognitive processing powers of the human brain including, but not limited to, symbolic cognitive architectures and inference process algebras;

means for housing at least one acoustical sensor, at least one acoustical transmitter and at least one electronic processing component;

means for processing and digitizing raw acoustical data received from at least one acoustical sensor and at least one acoustical transmitter;

means for receiving digitally processed acoustical and non-acoustical inspection data and fusing the inspection data for the purpose of generating additional metadata;

means for providing a database of diagnostic signatures including, but not limited to, acoustical, ultrasound, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection signatures) that characterize conditions being diagnosed;

means for performing cognitive analysis of fused inspection data and interpreting the results against a database of inspection signatures characterizing conditions being diagnosed, with the ability to anticipate abnormal conditions that fall outside inspection signature patterns contained within the database; and means for enabling at least one operator to analyze, interpret and manage the inspection process.

2. The cognitive medical and industrial inspection system and method in accordance with claim 1, wherein said means for performing cognitive analysis of fused inspection data through the use of mathematical techniques that emulate the cognitive processing powers of the human brain including, but not limited to, symbolic cognitive architectures and inference process algebras resulting in a cognitive diagnosis of the medical patient or industrial object being inspected comprises a software, firmware, hardware and combinations thereof cognitive diagnostics engine.

3. The cognitive medical and industrial inspection system and method in accordance with claim 1, wherein said means for housing at least one acoustical sensor, at least one acoustical transmitter and at least one electronic processing component comprises an acoustical system housing.

4. The cognitive medical and industrial inspection system and method in accordance with claim 1, wherein said means for processing and digitizing raw acoustical data received from at least one acoustical sensor and at least one acoustical transmitter, comprises at least one electronic processing component, all housed within an acoustical system housing.

5. The cognitive medical and industrial inspection system and method in accordance with claim 1, wherein said means for receiving digitally processed acoustical and non-acoustical inspection data and fusing the inspection data for the purpose of generating additional metadata, comprises a software, firmware, hardware and combinations thereof data fusion and metadata generation module.

6. The cognitive medical and industrial inspection system and method in accordance with claim 1, wherein said means for providing a database of diagnostic signatures including, but not limited to, acoustical, ultrasound, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection signatures) that characterize conditions being diagnosed comprises a software, firmware, hardware and combinations thereof diagnostic signature database.

7. The cognitive medical and industrial inspection system and method in accordance with claim 1, wherein said means for performing cognitive analysis of fused inspection data and interpreting the results against a database of inspection signatures characterizing conditions being diagnosed, with the ability to anticipate abnormal conditions that fall outside inspection signature patterns contained within the database comprises a software, firmware, hardware and combinations thereof cognitive processing module.

8. The cognitive medical and industrial inspection system and method in accordance with claim 1, wherein said means for enabling at least one operator to analyze, interpret and manage inspection data that has been fused and processed by mathematical techniques that emulate the cognitive abilities of trained human operators comprises an operator interface.

9. A cognitive medical and industrial inspection system for providing cognitive inspection of medical patients and industrial objects, comprising:
- an acoustical system housing, for housing at least one acoustical sensor, at least one acoustical transmitter and at least one electronic processing component;
- a software, firmware, hardware and combinations thereof cognitive diagnostics engine, for performing cognitive analysis of fused inspection data through the use of mathematical techniques that emulate the cognitive processing powers of the human brain including, but not limited to, symbolic cognitive architectures and inference process algebras resulting in a cognitive diagnosis of the medical patient or industrial object being inspected;
- at least one acoustical data processor, for processing and digitizing raw acoustical data received from at least one acoustical sensor and at least one acoustical transmitter;
- a software, firmware, hardware and combinations thereof data fusion and metadata generation module, for receiving digitally processed acoustical data from at least one acoustical sensor, at least one acoustical transmitter, non-acoustical inspection devices and systems, and combinations thereof; and fusing the inspection data for the purpose of generating additional metadata;
- a software, firmware, hardware and combinations thereof diagnostic signature database, for providing a database of diagnostic signatures including, but not limited to, acoustical, ultrasound, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection signatures) that characterize conditions being diagnosed;
- a software, firmware, hardware and combinations thereof cognitive processing module, for performing cognitive analysis of fused inspection data through the utilization of mathematical techniques that emulate the cognitive processing abilities of the human brain including, but not limited to, symbolic cognitive architectures and inference process algebras; and interpreting the results against a database of acoustical, non-acoustical, and combinations thereof signatures characterizing conditions being diagnosed with the ability to also identify and anticipate abnormal conditions that fall outside inspection signature patterns contained within the database; and
- an operator interface, for enabling at least one operator to analyze, interpret and manage the inspection process.

10. The cognitive acoustical inspection system as recited in claim 9, further comprising:
At least one infrasound sensor, for detecting infrasound acoustics equal to and below 20 Hz housed within an acoustical system housing.

11. The cognitive medical and industrial inspection system as recited in claim 9, further comprising:
At least one audible sensor, for detecting audible acoustics between 20 Hz and 20 kHz housed within an acoustical system housing.

12. The cognitive medical and industrial inspection system as recited in claim 9, further comprising:
At least one ultrasound sensor and at least one ultrasound transmitter, for detecting and transmitting ultrasound acoustics greater than 20 kHz housed within acoustical system housing.

13. The cognitive medical and industrial inspection system and method as recited in claim 9, further comprising:
a source of non-acoustical inspection data from non-acoustical devices and system including, but not limited to, electrocardiography (EKG), computed-tomography (CT), single photon emission computed tomography (SPECT), positron emission tomography (PET), magnetic resonance imaging (MRI), electromagnetic testing (ET), magnetic particle inspection (MT or MPI), magnetic flux leakage testing (MFL), liquid penetrant, radiographic (x-ray and gamma ray), eddy-current testing, low coherence interferometry, and combinations thereof (i.e., multi-modality inspection data).

14. The cognitive medical and industrial inspection system of claim 9 wherein said operator interface is wireless.

15. A cognitive medical and industrial inspection method for providing cognitive acoustical inspection of medical patients and industrial objects, comprising the steps of:
Providing a human operator with a cognitive inspection system that emulates a diagnosis performed by multiple highly trained operators skilled in interpretation of inspection data collected from multiple acoustical, non-acoustical, and combinations thereof, inspection devices; thereby lowering costs, simplifying the initial inspection and diagnosis for medical patients and industrial objects and minimizing the possibility of false negative and false positive interpretations;
Collecting inspection data from at least one acoustical sensor, at least one acoustical transmitter, non-acoustical inspection devices and systems, and combinations thereof; and performing data fusion which generates additional metadata thereby providing an enhanced set of inspection data that is representative of the medical patient or industrial object;
Performing cognitive analysis of fused inspection data through the utilization of mathematical techniques that emulate the cognitive processing abilities of the human brain including, but not limited to, symbolic cognitive architectures and inference process algebras; and interpreting the results against a database of acoustical, non-acoustical, and combinations thereof, signatures characterizing conditions being diagnosed with the ability to also identify and anticipate abnormal conditions that fall outside inspection signature patterns contained within the database;

Displaying inspection data and results of the cognitive analysis to an operator by means of an operator interface enabling the operator to analyze, interpret and manage the overall inspection process.

16. The cognitive medical and industrial inspection system of claim 15 wherein said operator interface is wireless.

* * * * *